(12) United States Patent
Chen et al.

(10) Patent No.: US 10,085,943 B2
(45) Date of Patent: Oct. 2, 2018

(54) POLYMER, THERMOSENSITIVE CARRIER AND USE THEREOF

(71) Applicant: Institute of Nuclear Energy Research, Atomic Energy Council, Executive Yuan, R.O.C., Taoyuan (TW)

(72) Inventors: Po-Jung Chen, Taoyuan (TW); Mao-Chi Weng, Taoyuan (TW); Mei-Hui Wang, Taoyuan (TW); Chien-Chung Hsia, Taoyuan (TW)

(73) Assignee: INSTITUTE OF NUCLEAR ENERGY RESEARCH, ATOMIC ENERGY COUNCIL, EXECUTIVE YUAN, R.O.C., Taoyuan (TW)

( * ) Notice: Subject to any disclaimer, the term of this patent is extended or adjusted under 35 U.S.C. 154(b) by 0 days.

(21) Appl. No.: 15/268,933

(22) Filed: Sep. 19, 2016

(65) Prior Publication Data
US 2017/0119676 A1    May 4, 2017

(30) Foreign Application Priority Data

Oct. 30, 2015 (TW) .............................. 104135781 A

(51) Int. Cl.
| | | |
|---|---|---|
| A61K 9/20 | (2006.01) |
| A61K 9/00 | (2006.01) |
| A61K 31/337 | (2006.01) |
| C08G 81/00 | (2006.01) |
| C09D 5/26 | (2006.01) |
| C09D 187/00 | (2006.01) |
| A61K 41/00 | (2006.01) |
| A61K 9/51 | (2006.01) |

(52) U.S. Cl.
CPC .......... *A61K 9/2031* (2013.01); *A61K 9/0092* (2013.01); *A61K 9/2009* (2013.01); *A61K 9/5146* (2013.01); *A61K 31/337* (2013.01); *A61K 41/0028* (2013.01); *A61K 41/0052* (2013.01); *C08G 81/00* (2013.01); *C09D 5/26* (2013.01); *C09D 187/005* (2013.01)

(58) Field of Classification Search
CPC .. A61K 9/0092; A61K 9/2009; A61K 9/2031; A61K 31/337; A61K 41/0052; A61K 9/5146; A61K 41/0028; C08G 81/00; C09D 5/26; C09D 187/005
See application file for complete search history.

(56) References Cited

U.S. PATENT DOCUMENTS

2011/0288484 A1* 11/2011 Kendall .............. A61B 17/205
                                                                 604/173

OTHER PUBLICATIONS

Bae et al. ("Thermosensitive Pluronic Micelles Stabilized by Shell Cross-linking with Gold Nanoparticles," in Langmuir 2006, 22, 6380-6384).*
Devi et al. ("Poloxamer: A Novel Functional Molecule for Drug Delivery and Gene Therapy" in J. Pharm. Sci. & Res. vol. 5(8), 2013, 159-165).*

* cited by examiner

*Primary Examiner* — Blessing M Fubara
(74) *Attorney, Agent, or Firm* — Locke Lord LLP; Tim Tingkang Xia, Esq.

(57) ABSTRACT

Disclosed herein are a novel polymer, a thermosensitive carrier prepared using the same and use thereof. The novel polymer is essentially composed of a PEO-PPO-PEO block copolymer and silane.

4 Claims, 7 Drawing Sheets

POLYMER, THERMOSENSITIVE CARRIER AND USE THEREOF

CROSS REFERENCE TO RELATED APPLICATION

This application also claims priority to Taiwan Patent Application No. 104135781 filed in the Taiwan Patent Office on Oct. 30, 2015, the entire content of which is incorporated herein by reference.

BACKGROUND

At present, the cancers are treated mainly through surgery, chemotherapy, and radiotherapy, but all of which suffer from drawbacks. In clinic, the tumor cells cannot be completely removed by surgical operations in most cases, thus leading to potential reoccurrence of tumors in the patients. Moreover, the chemo- and radiotherapy generally cause extremely serious side effects to normal tissues. Therefore, photothermal therapy gradually becomes prevalent.

Photothermal therapy is a technique in which a photothermal therapeutic material in a subject is irradiated by IR light at a wavelength that strongly penetrates the tissues of the subject, such that the light energy is absorbed by the material and converted into heat energy, whereby the cancer cells are killed by utilizing the heat energy. Moreover, due to the focusing characteristics of the light, the damage to normal tissues peripheral to the cancer or tumor tissues can be effectively reduced, thereby decreasing the side effects.

Besides, cocktail therapy is frequently used in clinic in the treatment of tumors, and multiple therapies are used to improve the cancer treatment effect. For instance, the photothermal therapy is used in combination with the chemo- or radiotherapy to achieve a dual therapeutic efficacy and significantly reduce the occurrence of drug resistance of tumor cells in a subject.

Currently, when the photothermal therapy is used in combination with the chemotherapy, the photothermal therapy may be effected by using various morphologies of nano-gold, for example, gold nanorods, gold nanoshells, and gold nanoboxes, and the chemotherapy may be effected by using common anti-cancer agents, for example, paclitaxel, camptothecin, and anthracycline. The two ingredients are combined with each other, to form a photothermal chemotherapeutic carrier. However, in practical use, some important issues exist. Because a majority of chemotherapeutic agents are lipid soluble and cannot be administered to animals by intravenous injection, they must be orally taken or carried by means of entrapment. Moreover, the release from the photothermal therapeutic pharmaceutical carrier is also limited. During intravenous injection, due to the existence of concentration gradient, the chemotherapeutic agent is naturally released from many pharmaceutical carriers in the prior art before reaching to the tumors. As a result, unwanted side effects are caused, the drug concentration arrived at the tumors is reduced, and controlled release of the drug cannot be achieved. Furthermore, surface modification of the nano-gold is complex and time-consuming. Although nano-gold has a high photothermal effect, the synthesized nano-gold has the disadvantages of high toxicity and low biological compatibility, and should undergo surface modification before use in a subject.

In view of this, there is an urgent need in the art for an improved thermosensitive pharmaceutical carrier, to overcome the disadvantages in the prior art.

SUMMARY

To make the essence of the disclosure clear, the summary provides brief description of the disclosure. The summary is not elaborated description of the present disclosure, and not intended to define the technical feature or scope of the present invention.

An aspect of the present disclosure relates to an organic/inorganic amphilic thermosensitive polymer having a structure as shown in Formula (1):

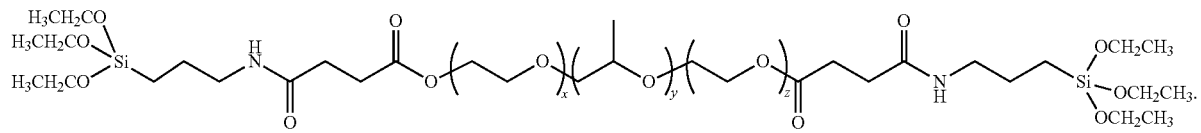

(1)

Another aspect of the present disclosure relates to a method for preparing a polymer as shown in Formula (1). The method comprises the steps of:

a) mixing a PEO-PPO-PEO block polymer with N-methyl-2-pyrrolidone, succinic anhydride, and 4-(dimethyl-amino)pyridine (DMAP), and reacting, to afford a PEO-PPO-PEO block polymer-carboxylate; and b) mixing the PEO-PPO-PEO block polymer-carboxylate with thionyl chloride, triethyl amine (TEA) and 3-aminopropyltriethoxysilane (APTES), and reacting, to afford the compound of Formula (1).

In an embodiment, the temperature is required to be raised to 50° C. in Step a) of the method described in the present invention, and the reaction is carried out under a nitrogen atmosphere. In a preferred embodiment, the temperature is required to be raised to 60° C. in Step a).

According to a specific embodiment of the present disclosure, the PEO-PPO-PEO block polymer is F127.

A further implementation of the present disclosure relates to a thermosensitive carrier. The carrier comprises a nano gold and an outer coating entrapping the nano gold. The outer coating is composed of the organic/inorganic amphilic thermosensitive polymer as shown in Formula (1).

In a specific embodiment of the present disclosure, the nano gold is gold nanorods.

In a further embodiment, the thermosensitive carrier further comprises a pharmaceutical composition entrapped by the outer coating. In a specific embodiment, the pharmaceutical composition is an anti-cancer agent, for example a lipid soluble anti-cancer agent.

Another aspect of the present disclosure relates to use of the thermosensitive nano gold carrier shown in any one of the above embodiments in the preparation of drugs for treating cancers.

The central idea, the technical means adopted, and various implementations of the present invention may be well understood by those of ordinary skill in the art of the present invention.

BRIEF DESCRIPTION OF DRAWINGS

To make the above and other objectives, features, advantages, and embodiments of the present invention more apparent, the present invention is described with reference to accompanying drawings, in which.

DETAILED DESCRIPTION OF DISCLOSED EMBODIMENTS

Figure 1:
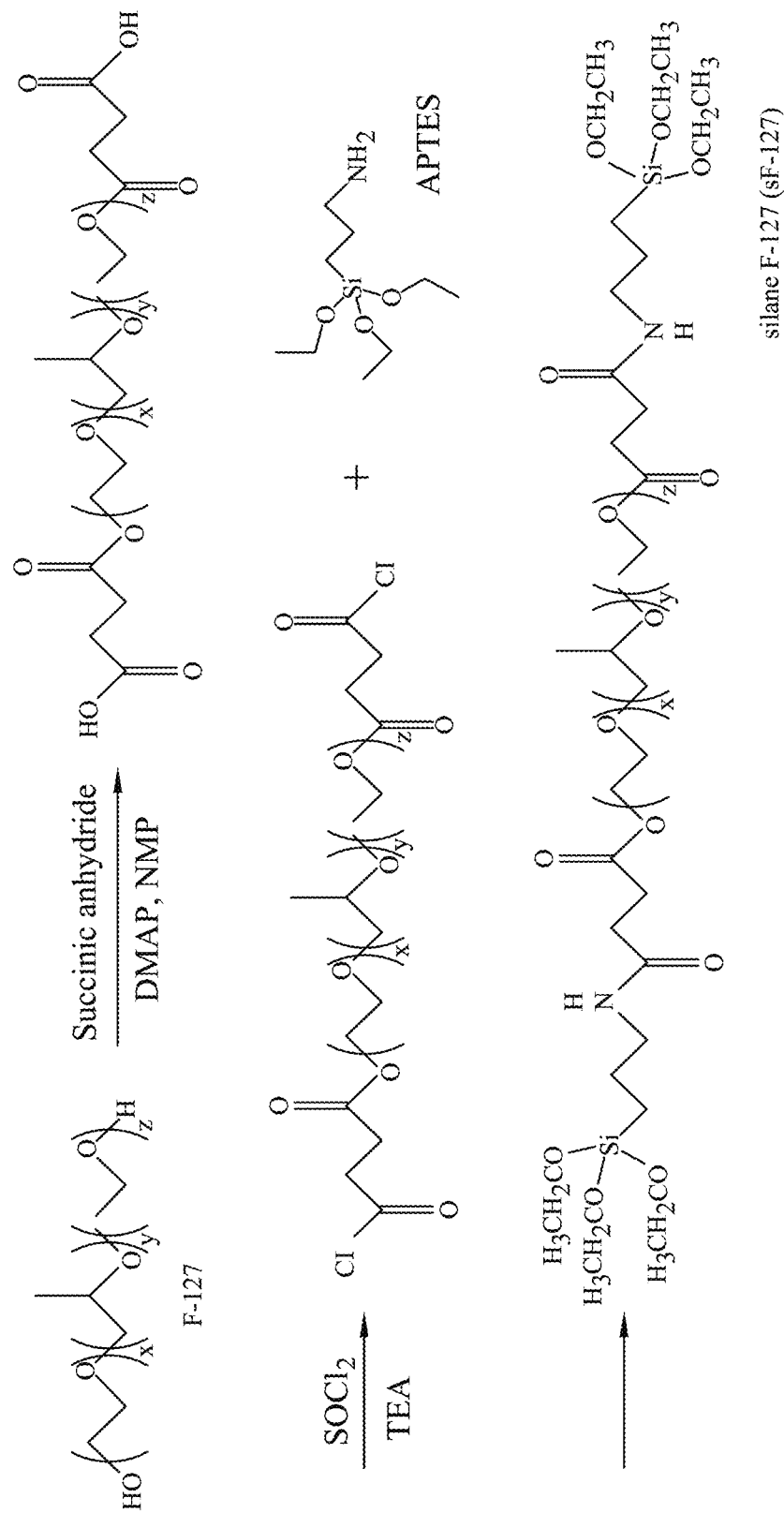
FIG. 1 is a flow chart of a method for synthesizing the present polymer according to an embodiment of the present invention.

To make the description of the present disclosure more thorough and complete, the implementations and specific embodiments of the present invention are exemplarily described hereinafter. However, the implementations and specific embodiments of the present invention are not limited thereto.

Unless otherwise stated, the scientific and technical terms used in the specification have the same meaning as commonly understood by those of ordinary skill in the art. Moreover, the referent used in the specification may be singular or plural, unless otherwise indicated.

The term "subject" or "patient" refers to an animal that can receive the thermosensitive carrier of the present invention. In a preferred embodiment, the animal is a mammal and particularly human.

The term "cancer" may be a non-solid or solid tumor. For example, the cancer includes, but is not limited to, leukemia, lymphoma, diaphysial osteosarcoma, multiple myeloma, testis carcinoma, thyroid cancer, prostate cancer, throat cancer, cervical cancer, nasopharyngeal cancer, breast cancer, colorectal cancer, pancreatic cancer, head and neck cancer, esophageal cancer, rectal cancer, lung cancer, liver cancer, brain cancer, melanoma or skin cancer.

As used in the specification, the term "about" generally means that the actual value is within ±10%, 5%, 1%, or 0.5% of a particular value or range. "About" indicates herein that the actual value falls within an acceptable standard error of the average, depending on the considerations of persons of ordinary skill in the art. Besides the case in the experimental examples, or unless stated specifically otherwise, it should be understood that the range, amounts, values, and percentages used herein are all modified by "about". Accordingly, unless stated otherwise, the values or parameters disclosed in the specification and appended claims are all rough values and may be changed as desired.

To solve the problem existing in the prior art, the present invention provides a new polymer and a thermosensitive carrier. In contrast to the prior art, the anti-cancer drugs and especially lipid soluble anti-cancer drugs can really be entrapped by the thermosensitive carrier prepared by using the new polymer material in the present invention. The thermosensitive carrier of the present invention can prevent the natural release of drugs entrapped in the carrier without the aid of additional materials, such that the drug release can be accurately controlled, thereby reducing the occurrence of side effects. Moreover, the thermosensitive carrier of the present invention can combine the chemotherapy and the thermal therapy together to produce a synergistic therapeutic effect, thus greatly increasing the tumor treatment efficiency. Meanwhile, the thermosensitive carrier of the present invention also has a good biocompatibility and a low toxicity.

Numerous examples are given below to illustrate various implementations of the present invention, whereby the technical contents disclosed in the present invention can be practiced by those of ordinary skill in the art based on the disclosure in the specification. Accordingly, the examples given below are not intended to limit the protection scope of the present invention. Furthermore, all the literatures cited in the specification are incorporated herein by reference in their entirety.

In the present disclosure, a controlled release thermosensitive carrier is formed by entrapping gold nanorods and a lipid soluble anti-cancer drug in a special organic/inorganic amphilic thermosensitive polymer, whereby light to heat conversion is effected by absorbing the laser by the gold nanorods, and the polymer deforms under compression with the heat energy, to press and release the anti-cancer drug. In this way, both the thermal therapy and the chemotherapy are achieved.

EXAMPLE 1

Synthesis of Polymer of the Present Invention

The main scheme for chemical synthesis in this example was shown in FIG. 1. The synthesis steps were as follows. The PEO-PPO-PEO block polymer used in this example was the F127 polymer (MW=12600). 10 g of F127 was dissolved in 100 ml of N-methyl-2-pyrrolidone (NMP), and then 0.2 g of succinic anhydride (SA) and 0.2 g of 4-(dimethyl-amino) pyridine (DMAP) were added and heated to about 60° C. The reaction was continued for 24 hrs under a nitrogen atmosphere, to obtain a product F127-carboxylate. Then, 0.2 ml of thionyl chloride, 0.2 ml of triethyl amine (TEA) and 0.3 ml of 3-aminopropyl triethoxysilane (APTES) were added and reacted for 24 hrs. After reaction, the product was extracted with ether (×3). In this manner, a —OH functional group on the F127 polymer was chemically converted into a —Si—OH functional group, and a silylated organic/inorganic amphilic thermosensitive polymer, that is, the polymer of the present invention (the structure as shown in Formula (1); referred to as Silane-127 hereinafter) was formed. After characterization by NMR and IR sepectrometry, the results are shown in FIGS. 2 and 3 respectively.

Figure 2:
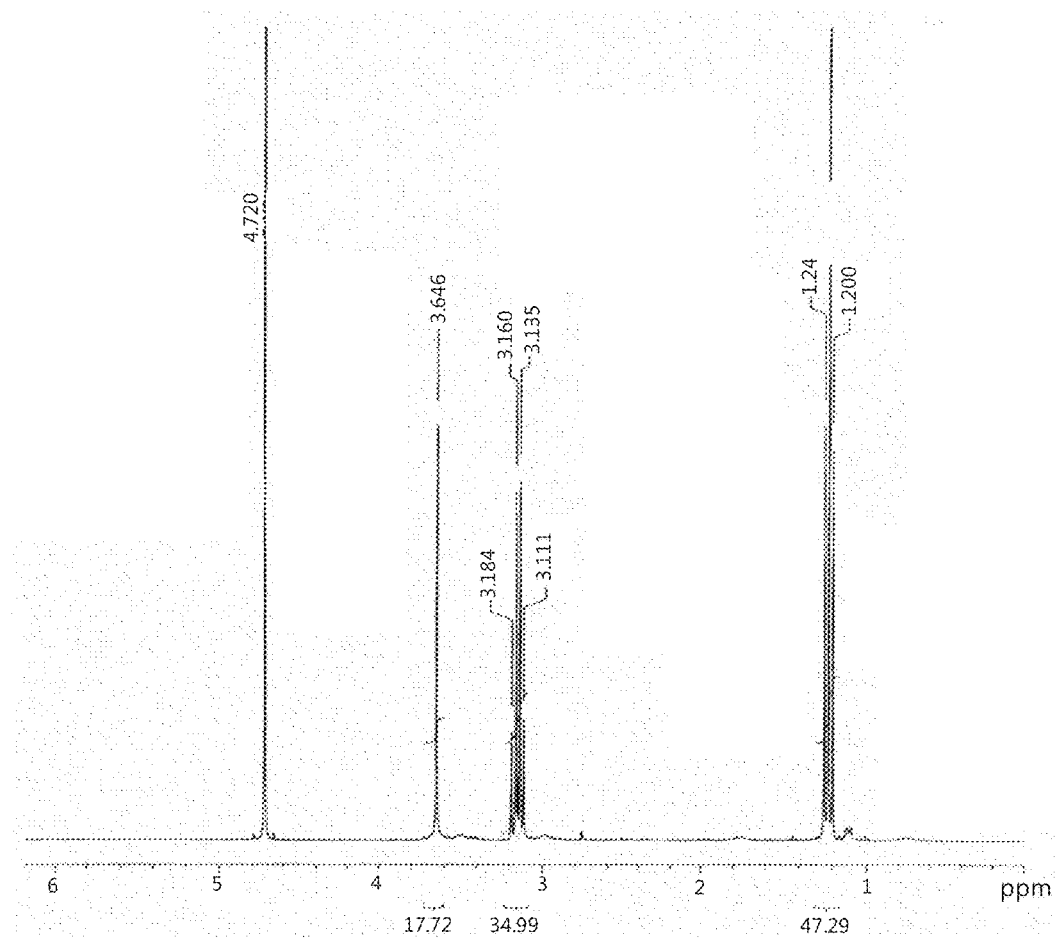
FIG. 2 is an NMR spectrum of the present polymer according to an embodiment of the present invention.
Figure 3:
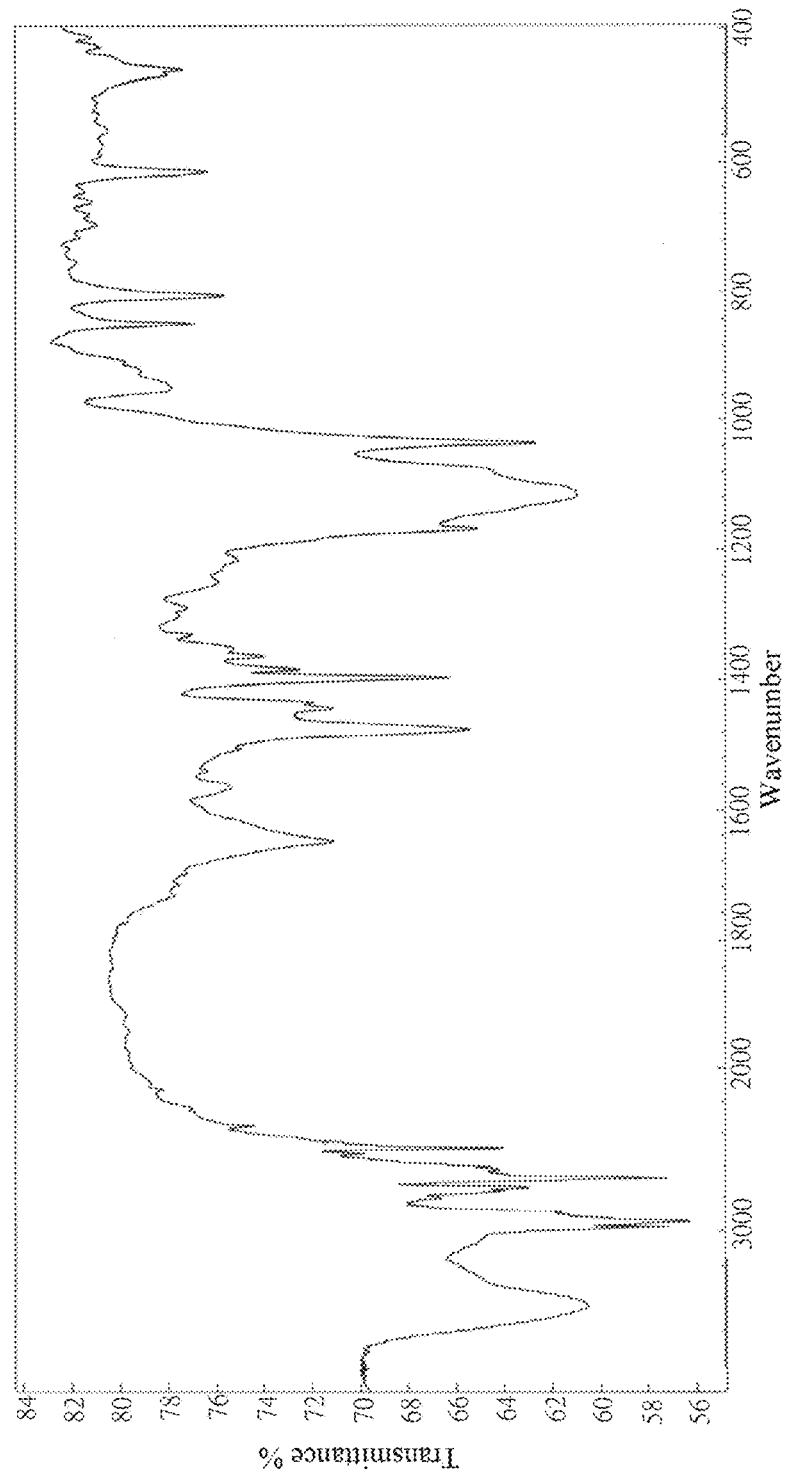
FIG. 3 is an IR spectrum of the present polymer according to an embodiment of the present invention.

FIG. 2 is a proton-NMR spectrum of silane-F127. It can be found from FIG. 2 that there are obvious shifts and additional peaks in the proton-NMR spectrum of the F127 polymer modified with silane. It can be inferred that the peak at 1.22 ppm is attributed to the contribution of the hydrogen atoms on —Si—O—CH2-CH3, and the peak at 4.7 ppm is attributed to the contribution of the hydrogen atoms on —CH2-CH2-O— in the F127 polymer. Furthermore, the change of function groups on silane-F127 compared with F127 is determined by IR sepectrometry in this example. The determination results are shown in FIG. 3. It can be found from FIG. 3 that the peak at 1100 $cm^{-1}$ is attributed to Si—OH and the peaks at 1650 $cm^{-1}$ and 1550 $cm^{-1}$ are attributed —CONH—. Based on the results from proton-NMR, carbon-NMR, and IR sepectrometry, the structure of the polymer silane-F127 according to the present invention can be determined.

EXAMPLE 2

Synthesis of Thermosensitive Carrier According to the Present Invention 2.1 Synthesis of Oil Soluble Gold Nanorods 0.3645 g of cetyltrimethyl-ammonium bromide (CTAB) was dissolved in 5 ml of deionized water, and stirred for 30 min. Then, 5 ml of $5\times10^{-4}$ M gold (III) chloride hydrate (HAuCl4) was added, and 0.6 ml of $1\times10^{-2}$ M sodium borohydride (NaBH4) was slowly added, upon which the color of the solution changed from clear yellow to clear brown, that is, the nano gold seeds were gradually formed. Finally, the formulated gold nanorod growth solution (1.385 g of cetyltrimethylammonium bromide (CTAB) dissolved in 38 ml of deionized water, 2 ml of $1\times10^{-2}$ M hydrogen tetrachloroaurate (III) trihydrate (HAuCl4), 0.4 ml of 0.1 M silver nitrate (AgNO3), and 0.22 ml of 1 M L-ascorbic acid) was added to the nano gold seed solution. After 24 h reaction, gold nanorods were produced. Then, cetyltrimethylammonium bromide (CTAB) on the surface of gold nanorods was removed and 300 µL of 1-octadecanethiol was added and reacted, to produce the oil soluble gold nanorods.

2.2 Synthesis of Controlled Release Thermosensitive Carriers (SFGRs)

Figure 4:
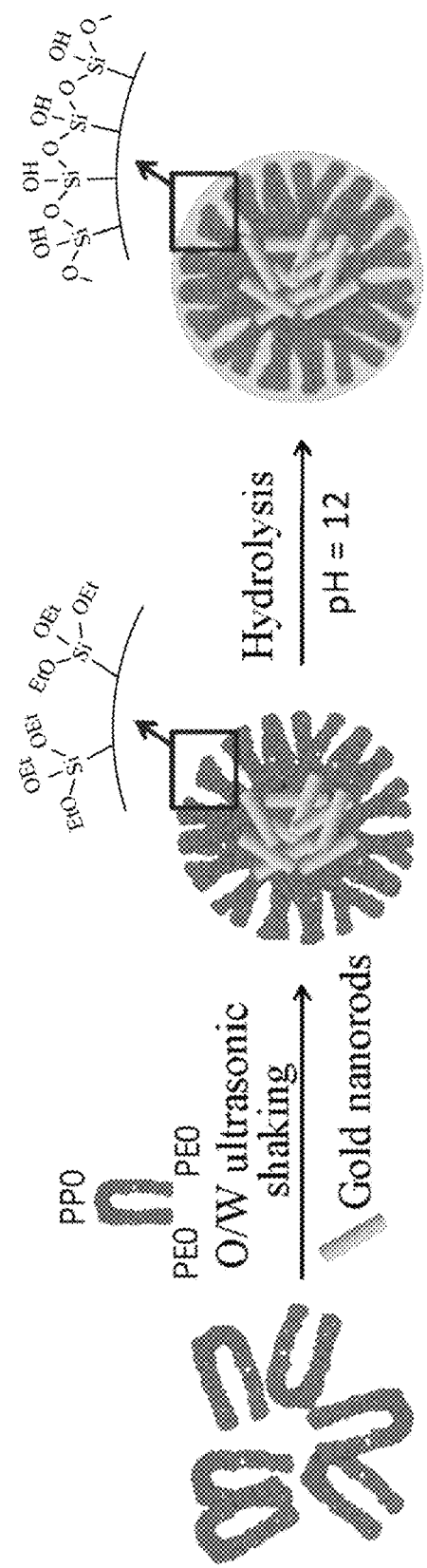
FIG. 4 is a flow chart of a method for preparing a thermosensitive carrier according to another embodiment of the present invention.

The main scheme for synthesizing the thermosensitive carrier in this example was shown in FIG. 4. A 2 wt % solution of the polymer silane-F127 was formulated in deionized water. Then, the 2 wt % solution of the polymer silane-F127 was evenly shaken for 3 min in an ultrasonic homogenizer together with the oil soluble gold nanorods and a lipid soluble anti-cancer drug (paclitaxel) dissolved in chloroform, upon which the solution was cloudy. Subsequently, the solution was transferred to a hot plate, heated to about 60° C., and magnetically stirred. After the oily solution was removed, the remaining solution was clear. The aqueous ammonia was added to subject the silyloxy group to hydrolysis and condensation. In this manner, the controlled release thermosensitive carrier of the present invention was obtained. The carrier was finally analyzed by transmission electron microscopy and dynamic light scattering.

Figure 5A:
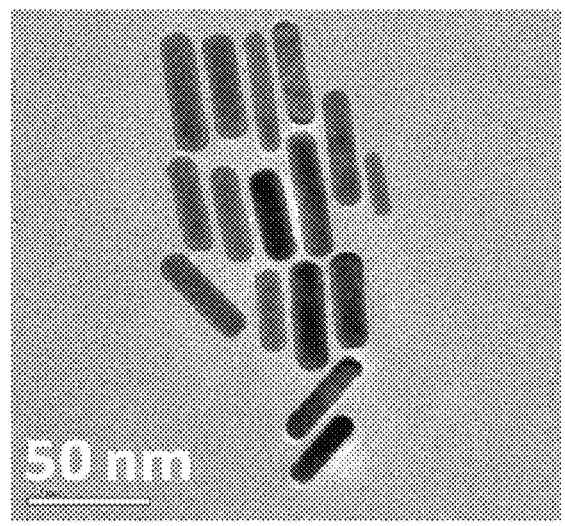
FIG. 5A is a transmission electron microscope (TEM) photo of the present gold nanorods.
Figure 5B:
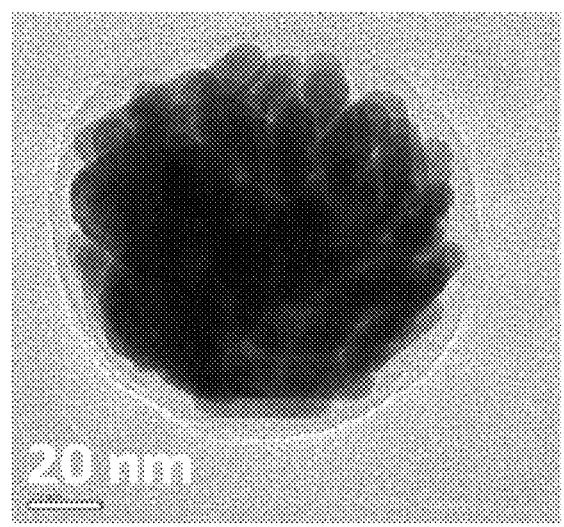
FIG. 5B is a TEM photo of the present thermosensitive carrier.
Figure 6:
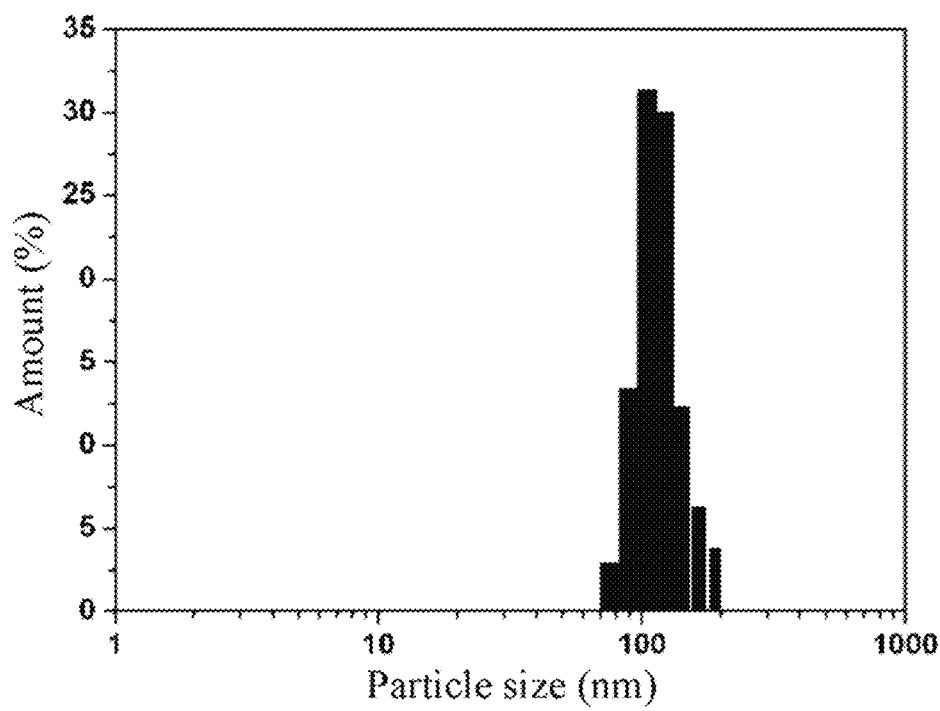
FIG. 6 shows results of dynamic light scattering of the thermosensitive carrier according to an embodiment of the present invention.

FIGS. 5A and 5B are TEM photos of the gold nanorods and thermosensitive carrier according to the present invention respectively. It can be clearly seen from the photo in FIG. 5B that the thermosensitive carrier does entrap the gold nanorods, and a layer of silicon oxide is formed on the surface. The results of dynamic light scattering show that the thermosensitive carrier of the present invention has a particle size of about 120 nm, as shown in FIG. 6.

EXAMPLE 3

Drug Release Profile of the Thermosensitive Carrier According to the Present Invention The thermosensitive carrier prepared in Example 2 was used in this example for determining the drug release profile. The results show that the thermosensitive carrier entrapping the anti-cancer drug has an excellent entrapment effect, and the drug cannot be naturally released.

Figure 7:
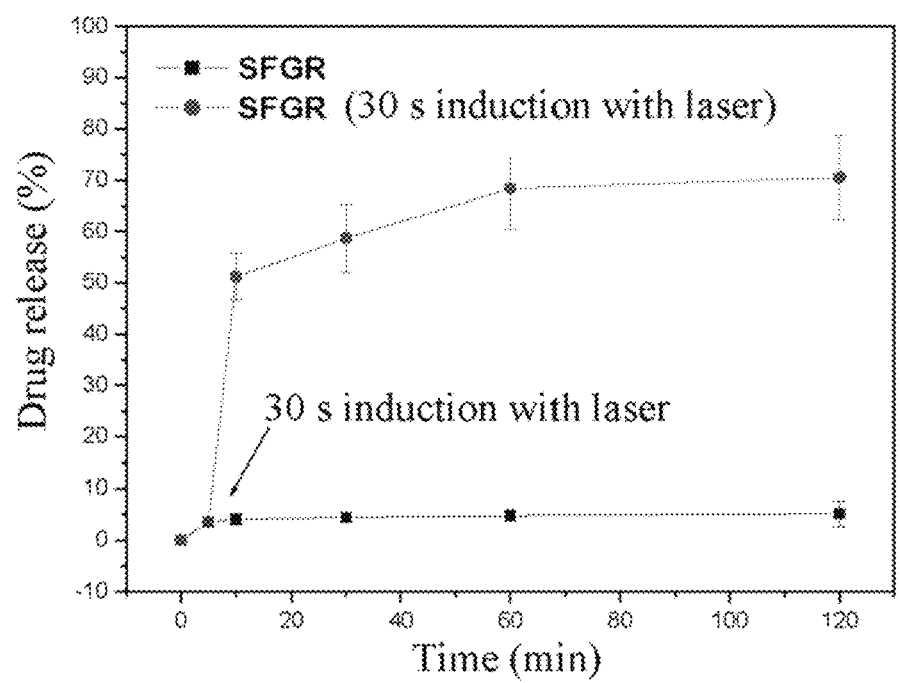
FIG. 7 shows a drug release profile of the present controlled release thermosensitive carrier according to an embodiment of the present invention with or without irradiation with laser at 808 nm.

The paclitaxel concentration released was measured by HPLC and calculated. Before irradiation with laser at 808 nm is administered, the drug molecules are well entrapped (no more than 5% of the drug is naturally released), and the carrier is useful as a system for long-term entrapment of the drug. However, after 30 s-irradiation with laser at 808 nm is administered, an absorption peak of the drug molecules can be immediately detected by HPLC. It is found from calculation that up to 70% of the drug is released, suggesting that after irradiation with laser, the light energy is absorbed and converted into heat energy by the thermosensitive carrier of the present invention, such that the thermosensitive polymer is contracted and compressed, to release the drug. The drug is released rapidly, to achieve a controlled release effect, as shown in FIG. 7.

EXAMPLE 4

Figure 8A:
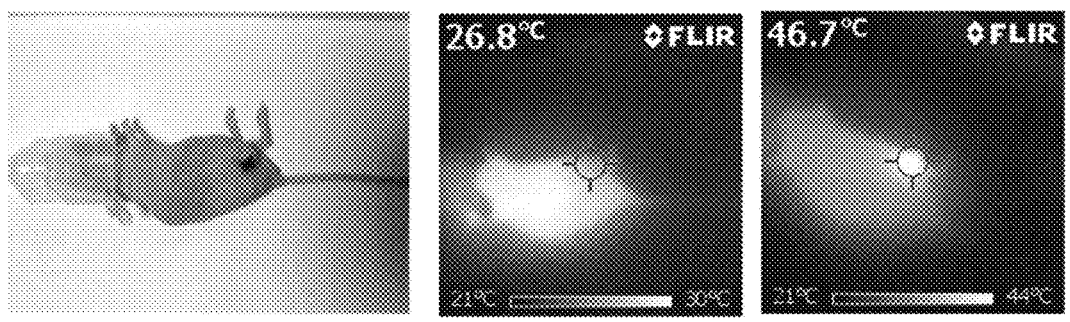
FIG. 8A shows results of temperature increment measured after the present controlled release thermosensitive carrier is injected into mice with tumors via the tail vein and the tumor site is irradiated for 30 s with laser at 808 nm according to an embodiment of the present invention.

Efficacy of the Thermosensitive Carrier According to the Present Invention in Animal Model of Tumor The thermosensitive carrier prepared in Example 2 was intravenously injected into mice xenografted with A549 human lung cancer cells, and circulated for 12 hrs in the mice. Continuous 30 s-irradiation with laser at 808 nm was administered at the tumor site. The results are shown in FIG. 8A.

Figure 8B:
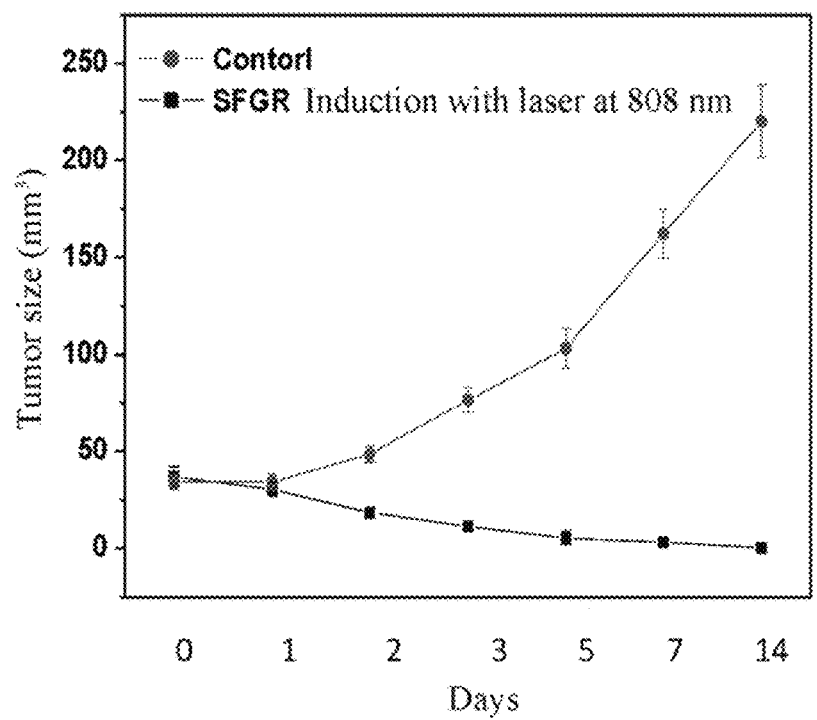
FIG. 8B shows a growth profile of a tumor in 14 days after irradiation with laser at 808 nm is administered to the tumor site as shown in FIG. 8A.

Thermal effect is produced at the tumor site immediately in the mice administered with the thermosensitive carrier of the present invention. It is found from consecutive 14 days observation after the 30 s-irradiation with laser at 808 nm is administered at day 1 that the tumors of the mice almost disappear completely, and the calculation result of the tumor volume is shown in FIG. 8B.

The results of this experimental example confirm that the thermosensitive carrier of the present invention can accurately control the drug release, deliver the drug precisely to the tumor site, and effectively reduce the tumor size in the animal model, thus having a significant therapeutic effect.

It can be known from the results obtained in all the examples above that the thermosensitive carrier of the present invention has an efficient thermal therapeutic effect in-vitro and in-vivo. Meanwhile, the thermosensitive carrier of the present invention may be loaded with, and effectively control the release of an anti-cancer drug.

The specific examples disclosed above are not intended to limit the protection scope of the present invention. Modifications may be made by those of ordinary skill in the art without departing from the principle and spirit of the present invention. Therefore, the scope of the present invention is defined by the claims.

What is claimed is:

1. A thermosensitive carrier, comprising:
a gold nanorod; and
an outer coating entrapping the gold nanorod, wherein the outer coating is comprised of an organic/inorganic amphilic thermosensitive polymer, having a structure as shown in Formula (1):

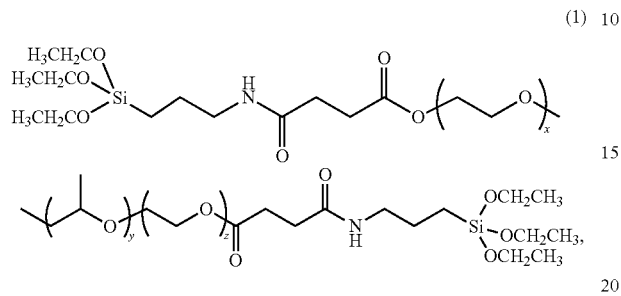

wherein the x is 98 y is 68, and z is 98.

2. The thermosensitive carrier according to claim 1, further comprising a pharmaceutical composition entrapped by the outer coating.

3. The thermosensitive carrier according to claim 2, wherein the pharmaceutical composition is an anti-cancer agent.

4. A method for treating cancer in a subject, comprising: administering to the subject a therapeutically effective amount of the thermosensitive carrier according to claim 2.

* * * * *